United States Patent [19]
Reiser et al.

[11] Patent Number: 5,347,040
[45] Date of Patent: Sep. 13, 1994

[54] SENSITIZED ONIUM SALTS

[75] Inventors: Arnost Reiser; Xiaohua He, both of Brooklyn, N.Y.

[73] Assignee: E. I. Du Pont de Nemours and Company, Wilmington, Del.

[21] Appl. No.: 988,435

[22] Filed: Dec. 9, 1992

[51] Int. Cl.$^5$ .................. C07C 69/017; C07C 301/00; C07C 301/02; C07F 9/40
[52] U.S. Cl. ..................... 560/139; 558/24; 558/25; 558/26; 558/59; 558/60; 558/160; 558/162; 558/158; 558/159; 562/52; 562/54; 562/46; 562/427; 562/432; 562/88; 562/89; 549/5; 549/16
[58] Field of Search .............. 568/1, 6, 14, 15, 29, 568/49, 44, 41; 558/24, 25, 26, 46, 47, 59, 60, 459, 158, 160, 162; 560/141, 194, 138, 140, 52, 54, 100, 102; 562/48, 68, 75, 76, 427, 426, 54, 88, 89, 41, 42, 431, 432, 46, 52; 549/16, 5; 564/306, 328, 305

[56] References Cited
U.S. PATENT DOCUMENTS
5,089,374  2/1992  Saeva .................... 430/271

*Primary Examiner*—Johann Richter
*Assistant Examiner*—Margaret J. Page

[57] ABSTRACT

Onium salt capable of generating acid upon exposure to actinic radiation having the following structure:

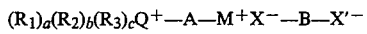

where:

Q is S;
$R_1$, $R_2$ and $R_3$ are independently substituted or unsubstituted aromatic, aliphatic, or aralkyl groups having 7-18 carbon atoms;
$M^+$ is a cationic organic radical;
A is a divalent radical selected from the group of hindered alkylene groups, substituted or unsubstituted aromatic or aralkyl groups;
B is a divalent aromatic sensitizer which absorbs radiation having a wavelength longer than 300 nm and is capable of transferring an electron to Q,
$x^-$ and $X'^-$ are anionic groups; and wherein A provides a spatial separation between Q and M, and B provides a spatial separation between X and X', such that the spatial separation provided by A between Q and M is substantially the same as the spatial separation provided by B between X and X'.

3 Claims, No Drawings

SENSITIZED ONIUM SALTS

FIELD OF THE INVENTION

This invention relates to novel salts containing onium cations which are capable of generating acid upon exposure to actinic radiation. More particularly, it relates to such salts which are sensitized to radiation using a sensitizer which is electrostatically linked to the onium cation.

BACKGROUND OF THE INVENTION

"Onium salts" are salts having the general formula $$R_aQ^+ An^-$$

where $An^-$ is a salt forming anion, R is aryl or alkyl, and Q is:
(1) a halogen and a=2;
(2) a group VIA element and a=3; or
(3) a group VA element and a=4.
The most common examples of these salts are the diaryl iodonium salts, the triaryl sulfonium salts and the tetraaryl phosphonium salts.

Onium salts are known to function as photoactivators for cationic polymerization and acid-degradation reactions, as disclosed, for example, in U.S. Pat. Nos. 4,136,101 and 4,603,101. Most of the onium cations absorb in the deep UV region, i.e., less than 300 nm, and therefore are only useful as initiators when activated by such short wavelength radiation. It is possible to alter the spectral response of the onium salt by the addition of a sensitizer, for example perylene, as disclosed in U.S. Pat. No. 4,603,101. The sensitizer absorbs radiation at a wavelength longer than that where the onium group absorbs and after absorption transfers an electron to the onium moiety. The effectiveness of the sensitizer depends upon is ability to interact directly with the onium salt. However, in most systems both the onium salt and the sensitizer are present in small amounts and the encounter probability of two low-concentration species is generally quite small.

To improve the effectiveness of sensitization, the onium salt must be kept in close spatial proximity to the sensitizer. One approach to accomplish this is to covalently tie the sensitizer to the central onium ion through one of the R groups. Such an approach has been disclosed by Pappas and Tilly [M. S. Tilly, Doctoral Dissertation, North Dakota State University, Fargo, N. Dak., October 1988] and in U.S. Pat. No. 5,047,568. These references disclose compounds having the general formula $$Ar\text{—}(\text{—}R_1\text{—})\text{—}S^+(R_2)(R_3)\ A^-$$

where Ar is a sensitizing aromatic group and $A^-$ is an anion. In the compound disclosed in Pappas and Tilly, Ar is 9-anthryl, $R_1$ is propyl, and $R_2$ and $R_3$ are phenyl.

A second approach to accomplish the spacial linkage of the sensitizer is to put the sensitizer in the anion so that the onium moiety and the sensitizer are held together by coulombic attraction. Such an approach has been disclosed in U.S. Pat. No. 4,772,530. In this reference, diphenyl iodonium, diphenylmethyl sulfonium, and triphenylmethyl phosphonium cations are paired with an anionic sensitizer which is a derivative of Rose Bengal.

In both of these prior art approaches, there is considerable flexibility in the linkage between the onium moiety and the sensitizer which allows the two moieties to assume a number of configurations. However, generally only one configuration will result in electron transfer to effect sensitization of the onium salt. Thus, the efficiency of these compounds is compromised by the flexibility and multiple configuration possibilities. In general, the quantum yields of reactions using these compounds are significantly less than 1.0.

There exists, therefore, a need for a sensitized onium salt in which the onium moiety is linked to the sensitizing moiety in such a way as to obtain more effective sensitization of the onium moiety.

SUMMARY OF THE INVENTION

The need for the above-described onium salt with more effective sensitization is met by the present invention, which provides an onium salt capable of generating acid upon exposure to actinic radiation having the following structure:

$$(R_1)_a(R_2)_b(R_3)_cQ^+\text{—}A\text{—}M^+\ X^-\text{—}B\text{—}X'^-$$

where:
Q is I, S or P;
$R_1$, $R_2$ and $R_3$ are independently aromatic groups having 6–12 carbon atoms, which may be substituted with hydroxyl, alkoxyl, amino or alkylamino groups; or aliphatic groups having 1–12 (preferably 1–4) carbon atoms, which may be substituted with hydroxyl, alkoxyl, amino or alkylamino groups; or aralkyl groups having 7–18 (preferably 7–10) carbon atoms, which may be substituted with hydroxyl, alkoxyl, amino or a alkylamino groups;
$M^+$ is a cat ionic organic radical;
A is a divalent radical selected from the group of hindered alkylene groups having 4–12 carbon atoms; aromatic groups having 6–18 (preferably 12–18) carbon atoms, which may be substituted with hydroxyl, alkoxyl, amino or alkylamino groups; and aralkyl groups having 7–24 (preferably 7–18) carbon atoms, which may be substituted with hydroxyl, alkoxyl, amino or alkylamino groups;
B is a divalent aromatic sensitizer which absorbs radiation having a wavelength longer than 300 nm and is capable of transferring an electron to Q,
$x^-$ and $X'^-$ are anionic groups; and
when
Q=I;
a=1
b and c=0
when
Q=S;
c=0
a and b=0, 1, or 2 such that a+b=2 when $R_1$ and $R_2$ are monovalent radicals;
a+b=1 when $R_1$ or $R_2$ is a divalent radical;
when
Q=p;
a, b and c=0, 1, 2 or 3 such that a+b+c=3 when $R_1$, $R_2$ and $R_3$ are monovalent radicals;
a+b+c=2 when one of $R_1$, $R_2$ or $R_3$ is a divalent radical; and
wherein A provides a spatial separation between Q and M, and B provides a spatial separation between X and X', such that the spatial separation provided by A between Q and M is substantially the same as the spatial separation provided by B between X and X'.

DETAILED DESCRIPTION OF THE INVENTION

In the onium salts of the invention, the sensitizer is built into the anionic portion of the salt. Each of the anionic sensitizer portion and the onium cation portion of the salt have two ionic moieties separated by a fairly rigid spacing group. This results in a limited number of possible configurations of the salt portions. In addition, the most favorable or only physical configuration is the one in which electron transfer is favored. The spacing group in the anionic portion of the salt also acts as the sensitizer for the onium moiety. Furthermore, the spacing groups in the anion and cation are substantially the same size so that the spacing between positively-charged moieties in the cation portion is substantially the same as the spacing between negatively-charged moieties in the anion portion.

The onium cation portion of the sensitized salts of this invention has the structure $$(R_1)_a(R_2)_b)\ (R_3)_c Q^+ \text{---} A \text{---} M^+$$

where Q represents the central atom in the onium moiety and is selected from the group consisting of iodine, sulfur and phosphorus. Although halogens and Group VIA elements are also known to form onium salts, the salts of real utility are based on the elements listed above. It is preferred that Q be sulfur. The sulfonium salts are more stable and produce more acid.

$R_1$, $R_2$ and $R_3$ are independently aromatic groups having 6-12 carbon atoms, aliphatic groups having 1-12 (preferably 1-4) carbon atoms, or aralkyl groups having 7-18 (preferably 7-10) carbon atoms. Any of these groups may be substituted with hydroxyl, alkoxyl, amino or alkylamino groups. When Q is iodine the R groups are monovalent. When Q is sulfur or phosphorus the R groups can be either monovalent or divalent, i.e., having two bonds to the central Q atom. The values for a, b, and c, depend on the central onium atom, Q, and on the nature of the R groups:

when
Q=I;
a=1
b and c=0
when
Q=S;
c=0
a and b=0, 1, or 2 such that a+b=2 when $R_1$ and $R_2$ are monovalent radicals;
a+b=1 when $R_1$ or $R_2$ is a divalent radical;
when
Q=p;
a, b and c=0, 1, 2 or 3 such that a+b+c=3 when $R_1$, $R_2$ and $R_3$ are monovalent radicals;
a+b+c=2 when one of $R_1$, $R_2$ or $R_3$ is a divalent radical.

Examples of suitable monovalent R groups include carbocyclic aromatic groups such as phenyl, alkyl-substituted phenyl and alkoxy-substituted phenyl; fused ring aromatics such as naphthyl groups; heterocyclic aromatic groups such as pyridyl; straight chain and branched alkyl groups; and arylalkyl groups such as benzyl. Examples of suitable divalent R groups include aliphatic groups bonded to the Q atom so as to form 5- and 6-membered rings, and substituted and unsubstituted biphenyls attached at the 6 and 6' positions. Preferred R groups include phenyl, methoxyphenyl, and methyl.

The M group is a cationic moiety and comprises the second positively-charged moiety of the onium cation portion. The M group should form a stable salt with the anionic portion of the sensitized salt, and should not interfere with the photoinduced reactions of the onium moiety. The M group can itself be an onium group, with either the same or different central cation, i.e., it can have the structure $$Q'^+(R_4)_d(R_5)_e(R_6)_f$$

where:
Q' is I, S or P;
$R_4$, $R_5$ and $R_6$ are the same as $R_1$, $R_2$ and $R_3$ above; and
when
Q'=I;
d=1
e and f=0
when
Q'=S;
f=0
d and e are 0, 1, or 2 such that d+e=2 when $R_4$ and $R_5$ are monovalent radicals;
d+e=1 when $R_4$ or $R_5$ is a divalent radical;
when
Q'=p;
d, e and f=0, 1, 2 or 3 such that d+e+f=3 when $R_4$, $R_5$ and $R_6$ are monovalent radicals; and
d+e+f=2 when one of $R_4$, $R_5$ or $R_6$ is a divalent radical.

Other examples of suitable M groups include ammonium, diazonium and oxonium moieties.

The A group is a divalent radical and functions as the spacing group between the two positively-charged moieties in the cationic portion of the sensitized salt. This group also provides most of the rigidity and spatial orientation in the cationic portion of the salt.

The A group should be stable to acid and non-reactive with the other groups in the salt. The A group can be a hindered alkylene group having 4-12 carbon atoms, aromatic group having 6-18 (preferably 12-18) carbon atoms, or an aralkyl group having 7-24 (preferably 7-18) carbon atoms. The A group may be modified with substituents, such as hydroxyl, alkoxyl, amino or alkylamino groups to provide improved handling properties, increased solubility, compatibility, synthetic advantages, etc., so long as the reactivity of the onium moiety is not substantially diminished.

It is preferred that the A group is an aromatic in order to provide a planar orientation for the cationic portion of the salt. Particularly preferred is 4,4'-biphenyl, i.e., a biphenyl group with the Q and M group bonded in the 4 and 4' positions.

It should also be noted that the size of the A group, that is the spacing it provides between the Q and M groups, should be matched to the size of the B group in the anionic portion of the salt. This will be discussed in greater detail below.

The anionic portion of the onium salt of the invention has the structure $$X^- \text{---} B \text{---} X'^-$$

which is the ionized form of the dibasic acid HX—B—X'H. X and X' can be any ionic groups which will function as at least a weak acid when protonated, and can be the same or different. Examples of suitable groups for X and X' include sulfate, sulfonate, sulfite, phosphate, phosphite, carboxylate, and the like. It is preferred that X and X' form a strong acid. A preferred group for X and X' is sulfonate.

The B group is a divalent aromatic radical which also contains the sensitization function for the onium cation. In order to be effective as a sensitizer, the B group must absorb radiation at a wavelength longer than the wavelength where the onium absorbs radiation and it must be able to transfer an electron to the onium moiety. In general, the B group will have significant absorption at wavelengths greater than 300 nm. The B group also functions as the spacing group between the two negatively-charged moieties in the anionic portion of the salt and provides most of the rigidity and spatial orientation thereto. The B group must therefore be selected based upon its sensitizing properties and its ability to spacially orient the two anionic moieties in close correlation to that achieved for the two cationic moieties by the A group.

Most groups which can provide both spectral sensitization and spacial orientation and rigidity will be aromatic, particularly fused aromatic systems. Examples of suitable aromatic groups include benzoflavin, anthracene, perylene, ruberene, benzophenone, anthraquinone, pyrene, anthrone and thioxanthone.

The B group can be modified with substituents to provide improved handling properties, increased solubility, compatibility, synthetic advantages, etc., as long as these do not substantially alter or diminish the sensitizing properties of the group. A preferred B group is a disubstituted anthracene group. Particularly preferred is 2,6-(9,10-diacetyloxyanthracene), i.e., 9,10-diacetyloxyanthracene with the X and X' groups bonded at the 2 and 6 positions.

As was mentioned previously, the size of the B group must be matched to the size of the A group, i.e., the spatial separation provided by the A group between the two cationic moieties should be substantially the same as the spatial separation provided by the B group between the two anionic moieties. The best physical correlation between the anion and the cation in the ion pair, and hence the most effective sensitization, will occur when A and B have the same size and provide substantially the same spatial separation. By "substantially the same" it is meant that the spatial separations differ by no more than about 25%. It is preferred that the difference be less than about 15%.

The onium salts of the invention can be used as photoactivators for cationic polymerization of materials such as epoxy and phenolic resins, vinyl monomers and oligomers, vinyl acetals, cyclic organic ethers, cyclic organic esters, cyclic organic amines, cyclic organic sulfides and organic silicon cyclics. They can also be used as photoactivators for the degradation or modification of compounds which have acid-labile or acid-reactive groups. In particular, polymeric compounds which have acid-labile groups in the polymeric backbone, in pendant groups or in crosslinkages can be used. Photosensitive compositions can be made comprising the onium salts of the invention and either materials which are susceptible to cationic polymerization or polymers having acid-labile groups. Such photosensitive compositions have applications as photoresists, lithographic printing elements, adhesives, printing inks, as well as many other uses.

EXAMPLES

EXAMPLE 1

This example illustrates the preparation of a bis sulfonium salt having an anthracene sensitizer in the anion.

A. Synthesis of disodium 9,10-diacetyloxy-anthracene-2,6-bisulfonate

Into a 125 ml round-bottom flask equipped with a condenser were placed 5 gm sodium anthraquinone-2,6-bisulfonate, 10 gm sodium acetate, 15 gm zinc dust and 60 gm acetic anhydride. The mixture was heated under reflux for a few minutes. The resulting solid was separated by filtering, added to 20 ml of acetic anhydride and heated for 10 minutes at 50° C. The solid was again separated by filtering, added to 20 ml methyl alcohol and heated for 10 minutes at 50° C. The solid was then removed by filtration, dried, and recrystallized from methyl alcohol.

B. Synthesis of 4,4'-diphenyl biphenylsulfide

Into a 250 ml three-necked round-bottom flask equipped with a magnetic stirrer, addition funnel and condenser were placed 30 ml dimethylformamide (DMF) and 1.8 g sodium hydride. The mixture was cooled to 0° C. in ice-water and then 8.5 g thiophenol was added dropwise. When the addition was complete, the mixture was brought to room temperature and, after standing for 2 hours, a solution of 4,4'-dibromobiphenyl in 30 ml DMF was added. The mixture was refluxed overnight, cooled to room temperature, and poured into ice water. After filtering, the water-insoluble fraction was recrystallized from hexanes.

C. Synthesis of 4,4,4',4'-tetraphenyl bis-sulfonium biphenyl hexafluoroantimonate Into a 25 ml single-necked flask equipped with a magnetic stirrer, a reflux condenser and a nitrogen bypass were placed 3.7 gm 4,4'-diphenyl-biphenylsulfide, 6.0 gm diphenyliodonium hexafluoroantimonate, and 0.1 gm copper benzoate. This mixture was heated for 3 hours at 120°-125° C. in an oil bath. After cooling, the semi-solid product was washed several times with ether to remove the iodated by-products. The main product was separated by column chromatography.

D. Conversion of disodium 9,10-diacetyloxyanthracene-2,6-bisulfonate to 9,10-diacetyloxyanthracene-2,6-bisulfonic acid 40 g of Dowex ® 50X8-100 ion exchange resin (Aldrich Chemical Co., Milwaukee, Wis.) was placed in 40 ml of a 10% by weight HCl solution and stirred overnight. The resin was then packed into a column. 100 ml of a 10% HCl solution was then slowly passed through the column. The column was washed with 300 ml water until no more acid emerged. 1.3 g of disodium 9,10-acetyloxy-anthracene-2-6-bisulfonate from step A was dissolved in a mixture of 80 ml water and 20 ml tetrahydrofuran (THF). This solution was passed through the column, which was then washed with a 4:1 (by volume) mixture of water and THF. The fraction containing the sulfonic acid collected.

E Conversion of 4,4,4',4'-tetraphenyl bis-sulfonium biphenyl hexafluoroantimonate to 4,4,4',4'-tetraphenyl bis-sulfonium biphenyl hydroxide 40 g of Dowex ® IX8-50 ion exchange resin (Aldrich Chemical Co., Milwaukee, Wis.) was placed in 40 ml of a 10% by weight NaOH solution and stirred overnight. The resin was then packed into a column and 100 ml of a 10% by weight NaOH solution slowly passed through the column. The column was then washed with water until no more ions emerged 2.6 g of the 4,4,4',4'-tetraphenyl bis-sulfonium biphenyl hexafluoroantimonate from step C was dissolved in a mixture of 80 ml THF and 20 ml water. This solution was passed through the prepared column, which was then washed with a 4:1 (by volume) mixture of THF and water. The fraction containing the disulfonium dihydroxide, as identified by UV spectrum and pH, was collected.

F. Synthesis of 4,4,4',4'-tetraphenyl bis-sulfonium biphenyl 9,10-diacetyloxyanthracene 2,6-bisulfonate.

The solutions resulting from the ion exchange in steps D and E were combined. THF was removed by evaporation and the product crystallized from a 4:1 mixture of acetonitrile and methyl alcohol.

EXAMPLE 2

This example illustrates the high quantum yield of acid generation using the onium salt from Example 1.

A dilute solution ($5\times10^{-4}$ M) of the bis sulfonium salt from Example 1 was prepared in a 3:1 (by volume) mixture of dichloromethane and methanol. This solution was exposed to radiation from a 150 W mercury lamp at 365 nm at a distance of 10 cm for 1 minute. The amount of acid generated was determined by the bleaching of an indicator dye as described by McKean, Schaedeli and MacDonald in ACS Symposium Series No. 412, 1989, p.27. The quantum yield of acid formation was found to be 0.82.

Comparative Examples 1-4

In these examples the quantum yield of acid formation was determined for different sulfonium compounds for comparison with the sulfonium salt of the invention.

Comparative Example 1

A dilute solution ($5\times10^{-4}$ M) of triphenyl-sulfonium hexafluoroantimonate without a sensitizer was prepared in dichloromethane and treated as described in Example 2, except that the solution was irradiated at 254 nm. The quantum yield of acid formation was determined as described in Example 2, and is given in Table 1.

Comparative Example 2

Comparative Example 1 was repeated with the addition of anthracene to a concentration of $5\times10^{-4}$ M. The anthracene was not bound to the sulfonium salt. The solution was irradiated at 365 nm and the quantum yield of acid formation was determined as described in Example 2. The result is given in Table 1.

Comparative Example 3

A dilute solution ($5\times10^{-4}$ M) of a sulfonium salt having the formula Ar—$CH_2$—$CH_2$—$CH_2$—$S^+$(Ph)(Ph) $SbF_6^-$ (Ar=anthracene) was prepared in dichloromethane and irradiated at 365 nm as described in Example 2. The anthracene sensitizer was bonded to the sulfonium moiety with a flexible hydrocarbon linkage. The quantum yield of acid formation was determined as described in Example 2, and is given in Table 1.

Compartive Example 4

In this example the sulfonium moiety was bound to the anthracene sensitizer by electrostatic attraction in a salt having a single cationic moiety and a single anionic moiety.

The sulfonium salt was triphenylsulfonium 9,10-diacetyloxyanthracene-2-sulfonate. The sulfonate anion was prepared from anthraquinone-2-sulfonate in a procedure analogous to the preparation of 9,10-diacetyloxyanthracene 2,6-disulfonate described in Example 1. Using an ion exchange procedure analogous to that described in Example 1, the sulfonate anion was converted to the acid form (9,10-diacetyloxyanthracene-2-sulfonic acid) and the sulfonium ion was converted to the basic form (triphenylsulfonium hydroxide). These two were combined to form the final salt, triphenylsulfonium 9,10-diacetyloxyanthracene-2-sulfonate.

A dilute solution ($5\times10^{-4}$ M) of the salt was prepared in a 9:1 (by volume) solution of dichlormethane and methanol and irradiated at 365 nm as described in Example 2. The quantum yield of acid formation was determined as described in Example 2, and is given in Table 1.

TABLE 1

| Sample | Φ |
| --- | --- |
| Example 2 | 0.82 |
| Comparative Example 1 | 0.64 |
| Comparative Example 2 | 0.03 |
| Comparative Example 3 | 0.27 |
| Comparative Example 4 | 0.26 |

This table clearly illustrates the improved sensitization achieved in the sulfonium salts of the invention.

EXAMPLE 3

This example illustrates the generation of acid in films by the bis onium salt of the invention.

A solid film of poly(methylmethacrylate) containing 10% by weight of the bis sulfonium salt prepared in Example 1 was cast from solution onto a glass plate. The film was exposed to radiation using the same source and conditions as in Example 1. The exposed film was dissolved in dichloromethane and the amount of acid formed was determined in solution as described in Example 2. The quantum yield of acid formation in the film was found to be 0.49.

What is claimed is:

1. An onium salt capable of generating acid upon exposure to actinic radiation having the following structure:

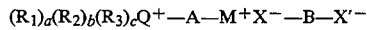

where:

Q is S;

$R_1$, $R_2$ and $R_3$ are independently aromatic groups having 6-12 carbon atoms, which may be substituted with hydroxyl, alkoxyl, amino or alkylamino groups; or aliphatic groups having 1-12 carbon atoms, which may be substituted with hydroxyl, alkoxyl, amino or alkylamino groups; or aralkyl groups having 7-18 carbon atoms, which may be substituted with hydroxyl, alkoxyl, amino or alkylamino groups;

$M^+$ is a cationic organic group having the structure:

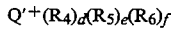

where Q' is S;

$R_4$, $R_5$, and $R_6$ are independently aromatic groups having 6-12 carbon atoms, which may be substituted with hydroxyl, alkoxyl, amino or alkylamino groups; or aliphatic groups having 1-12 carbon atoms, which may be substituted with hydroxyl, alkoxyl, amino or alkylamino groups; or aralkyl groups having 7-18 carbon atoms, which may be substituted with hydroxyl, alkoxyl, amino or alkylamino groups;

f=0;

d and e are 0, 1 or 2 such that d+e=2 when $R_4$ and $R_5$ are monovalent groups; and d+e=1 when $R_4$ or $R_5$ is a divalent group;

A is a divalent group selected from the group of hindered alkylene groups having 4–12 carbon atoms; aromatic groups having 6–18 carbon atoms, which may be substituted with hydroxyl, alkoxyl, amino or alkylamino groups; and aralkyl groups having 7–24 carbon atoms, which may be substituted with hydroxyl, alkoxyl, amino or alkylamino groups;

B is a divalent aromatic sensitizer which absorbs radiation having a wavelength longer than 300 nm and is capable of transferring an electron to Q, $X^-$ and $X'^-$ are anionic groups independently selected from the group consisting of sulfate, sulfonate, sulfite phosphate, phosphite and carboxylate; and when c=0;

a and b=0, 1, or 2 such that a+b=2 when $R_1$ and $R_2$ are monovalent groups;

and a+b=1 when $R_1$ or $R_2$ is a divalent group;

wherein A provides a spatial separation between Q and M, and B provides a spatial separation between X and X', such that the spatial separation provided by A between Q and M is substantially the same as the spatial separation provided by B between X and X'.

2. The onium salt of claim 1 wherein B is selected from the group consisting of anthracene, benzoflavin, perylene, ruberene, benzophenone, anthraquinone, pyrene, anthrone and thioxanthone.

3. The onium salt of claim 1 wherein $R_1$, $R_2$, $R_4$, and $R_5$ are phenyl groups; A is 4,4'-biphenyl; B is 2,6-(9,10-diacetyloxy anthracene); and $X^- = X'^- = SO_3^-$.

* * * * *